United States Patent [19]

Wohlgemuth

[11] Patent Number: 4,689,011
[45] Date of Patent: Aug. 25, 1987

[54] DENTAL PERCUSSION INSTRUMENT

[75] Inventor: Jürgen Wohlgemuth, Darmstadt, Fed. Rep. of Germany

[73] Assignee: Siemens Aktiengesellschaft, Berlin and Munich, Fed. Rep. of Germany

[21] Appl. No.: 802,244

[22] Filed: Nov. 27, 1985

[30] Foreign Application Priority Data

Dec. 13, 1984 [DE] Fed. Rep. of Germany ....... 3445529

[51] Int. Cl.⁴ ............................................. A61C 3/08
[52] U.S. Cl. .................................................. 433/121
[58] Field of Search ....................... 128/774, 776, 777; 73/82, 11, 12; 433/150, 32, 118, 119

[56] References Cited

U.S. PATENT DOCUMENTS 3,377,704  4/1968  Brodie et al. ....................... 433/118
4,482,324  11/1984  Wohlgemuth ....................... 428/776
4,499,906  2/1985  Wohlgemuth et al. .............. 128/776

FOREIGN PATENT DOCUMENTS 2617779  2/1982  Fed. Rep. of Germany .

Primary Examiner—Robert Peshock
Attorney, Agent, or Firm—Hill, Van Santen, Steadman & Simpson

[57] ABSTRACT

A dental percussion instrument, which has a instrument housing fashioned as a handpiece, a ram with a test head at one end being mounted in the housing for movement between a retracted and an extended position and an electromagnetic drive for shifting the ram between said positions, characterized by the ram having essentially a constant cross-section over its entire length, a permanent magnet being secured to the other end of the ram opposite the test head and the magnetic coil of the drive being rigidly situated in the instrument housing in a portion spaced axially from the other end of the ram and the permanent magnet.

14 Claims, 6 Drawing Figures

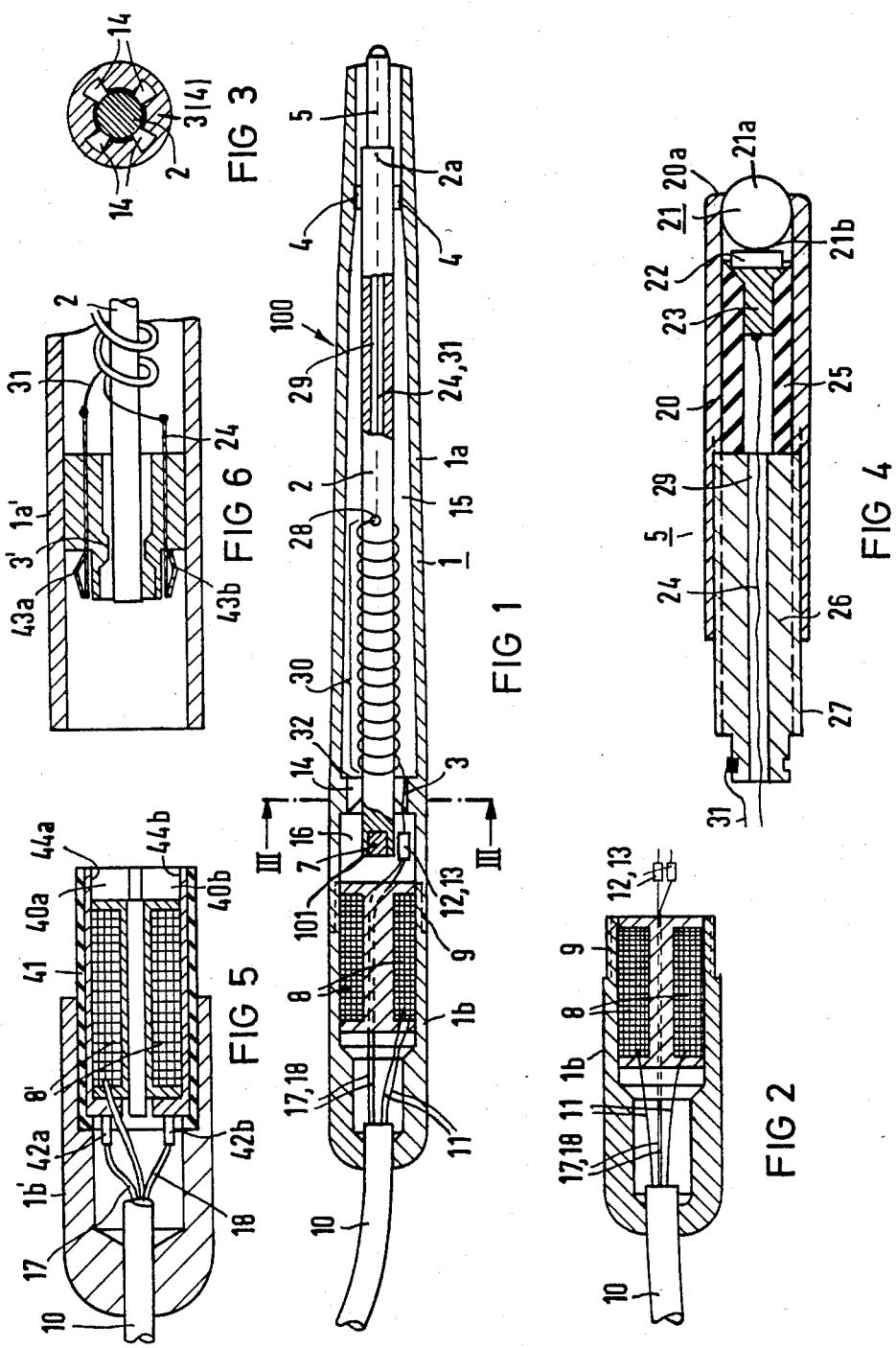

DENTAL PERCUSSION INSTRUMENT

BACKGROUND OF THE INVENTION

The present invention is directed to a dental percussion instrument comprising an instrument housing designed as a handpiece, a ram having a test head at one end and being mounted for axial movement in the instrument housing and an electromagnetic drive means for shifting the ram axially in the housing.

Percussion instruments are known. In one type, a compression spring is arranged concentrically relative to the ram to act as a drive means and this type is disclosed in German Pat. No. 26 17 779. In another type, a magnetic coil is the drive means for moving a ram in the housing and this type is disclosed in U.S. Pat. No. 4,499,906.

In order to meet the demands of being able to execute a reliable diagnosis with the instrument even at locations in the mouth of the patient which are relatively poorly accessible, a desired aim is to keep the instrument as slim as possible. Thus, it is desirable to have as small a diameter as possible precisely in the front region of the instrument which is where the drive is situated in the known structures.

Another problem is to move the ram with a constant speed after the drive has been shut off and until impact against the test subject occurs. Since the ram in the known instruments comprises a part having a considerable cross-sectional enlargement as seen over its length and this increased cross-sectional enlargement not only increases the diameter but also results in an undesirable braking effect, it is not possible to obtain the constant speed with the desired precision for the known instruments.

SUMMARY OF THE INVENTION

An object of the invention is to provide a percussion instrument which avoids the disadvantages of the cross-sectional size and non-constant speed during the period between turning off the drive and until impact. To accomplish these goals, the present invention is directed to an improvement in a dental percussion instrument having an instrument housing fashioned as a handpiece, a ram containing a test head at one end, means mounting the ram in the instrument housing for axial movement and electromagnetic drive means for shifting the ram axially within the housing between a retracted position and an extended position. The improvements are that the ram has essentially a constant cross-sectional construction over its entire length and has a permanent magnet mounted at another end facing away from the test head and wherein said drive means includes the permanent magnet and an electromagnetic coil which is mounted in the instrument housing in an axially spaced position relative to the other end of the ram and the permanent magnet.

Because the electromagnetic coil of the drive means is situated behind the other end of the ram and the ram itself has an essentially constant cross-section over its entire length, an instrument with an extremely small outside diameter can be achieved. This outside diameter is essentially defined only by the cross-section of the ram, the means for mounting the ram in the housing and the thickness of the walls of the housing.

The drive is advantageously formed by the permanent magnet being secured to a back end of the ram and by the magnetic coil lying axially behind this permanent magnet. Together with the back part of the instrument housing and the supply lines, the magnetic coil advantageously forms a structural unit which cannot be operationally separated and which is connected to the remaining instrument part by a suitable easily releasable connection, for example, a screw-type connection or a plug-type connection. The number of parting locations for the electrical lines, which are present in the previously known instruments of this type, if the instruments were to be constructed for disassembly, can be reduced by means of such an arrangement. This is meaningful for reasons of cleaning, repairing and other reasons.

The electrical connection of the lines, which must be conducted to the front part of an instrument, can advantageously occur by means of a suitable structural design of a flux-directing or concentrating ring or element which surrounds the drive coil. For example, the flux concentrating ring axially extends over the drive coil and is subdivided into two mutually insulated segments which extend parallel to the axis. These two segments are employed for contact transmission and cooperate with corresponding resilient cooperating contacts in the other handpiece part. Advantageously, the surface of this flux-directing ring is composed of a soft iron material and is coated at least in the region of the contacting with a suitable contact material which is selected from a group consisting of nickel, silver, gold, platinum and rhodium.

When the part of the instrument housing containing the drive coil has a length of a maximum of $\frac{1}{3}$ to $\frac{1}{4}$ of the overall length of the instrument, the instrument has favorable manipulation characteristics. In addition, because the part with the drive coil is connected to the supply lines, the separation of the parts is easier.

The ram is situated in the front part of the instrument housing and the mounting means comprise frictionless bearings. These are advantageously formed with one or more axial openings so that the neighboring chambers formed by the housing and the ram are in communication with one another for the exchange of air.

When, as a proposed additional advantageous development of the invention, the flexibly flaccid feed cable provided in the known percussion instruments, which connects the acceleration pickup to the measuring electronics, is replaced by a lead or line of electrically conductive, insulated wire which is wound spirally in a concentric fashion around the ram and has spring-elastic properties. Then one can also do with a minimum space requirement with respect to the line management. Over and above this, the employment of the helical spring, which is formed by the spirally wound wire, also has the advantage that a twisting or, respectively, looping of the cable is impossible and the danger of breaking the cable is avoided because of prevention of the looping or twisting of the cable. In addition, this design for the cable avoids damage to the insulation due to rubbing against the housing wall and thus avoids the instrument from becoming defective.

A helical spring can be advantageously composed of stranded wires having two twisted individual wires or of a coaxial line. In its loaded condition, the spring is advantageously compressed to such a degree that the force of its prestress corresponds to the frictional force and opposes this frictional force during the forward motion of the ram from the retracted position to the extended position. The prestressed path of the spring is thereby far, far greater than the stroke of the ram so that spring power remains approximately constant over the entire stroke of the ram. The undesirable frictional force of the bearings of the mounting means for the ram during the forward motion can thus be largely compensated by this spring element.

Additional advantages and objects will be readily apparent from the following description of the preferred embodiments and from the drawings.

BRIEF DESCRIPTION OF THE DRAWINGS

FIG. 1 is a longitudinal cross-sectional view of a dental percussion instrument in accordance with the present invention;

FIG. 2 is a longitudinal, cross-sectional view of a back part of the instrument of FIG.1;

FIG. 3 is a cross-sectional view taken along lines III—III of FIG. 1;

FIG. 4 is an enlarged longitudinal cross-sectional view of a test head of the device of FIG. 1;

FIG. 5 is an enlarged longitudinal cross-sectional view of an embodiment of the back or base part of the instrument of the present invention; and FIG. 6 is a partial longitudinal cross-sectional view of the front or forward instrument part utilized with the back part of FIG. 5.

DESCRIPTION OF THE PREFERRED EMBODIMENTS

The principles of the present invention are particularly useful when incorporated in a dental percussion instrument generally indicated at 100 in FIG. 1. The percussion instrument 100 includes an instrument housing 1, which has mounting means formed by bearings 3 and 4 for receiving or supporting in a largely friction-free manner an elongated ram 2. The housing 1 is about 150 mm long and about 15 mm thick. The ram 2 has a constant cross-section over its entire length and contains a test head 5 at its one end and at an opposite end or face 101 has a recess in which a permanent magnet 7 is mounted. A magnetic coil 8 is situated in the housing 1 adjacent to the permanent magnet 7 and is axially behind the permanent magnet 7. The magnetic coil 8 and the permanent magnet 7 form a drive for the forward and return motion of the ram 2.

The instrument housing 1 is divided by a screw-type connection 9 into a front part or section 1a and a back part or section 1b. As illustrated, the front section 1a contains the ram 2 with the permanent magnet 7 while the back section 1b contains the drive coil 8.

The back instrument section 1b is shown as a discrete part in FIG. 2. The drive coil 8 is an integral component of the housing part 1b and is advantageously rigidly connected to a supply hose or line 10. Given a change of the front instrument part 1a, for example, for the purpose of cleaning, sterilizing or for some other purpose, the electrical lines or lead 11 leading to the drive coil 8 need not be separated and thus only plug-type connectors 12 and 13 for connecting lines or leads 17 and 18 to lines or leads 24 and 31 whose purposes shall be explained later need be provided to enable separation at the parting location.

The means for mounting the ram 2 are two bearings 3 and 4 which are designed as sliding bearings which in accordance with the sectional view of FIG. 3, has a plurality of radially inwardly extending ridges separated by axial openings 14. The axial openings 14 of the bearing 3 allow the movement of air between a chamber 15 which is separated by the bearing 3 from a chamber 16, which chambers are formed between an inner wall surface of the housing 1 and the ram 2. Air movement between these chambers 15 and 16 can thus compensate for movement of the ram 2.

The test head 5, which is best illustrated in FIG. 4, is formed by an outer sleeve 20 which at a front end 20a has a slight constriction. A ball 21, which serves as the impact member, is received in the sleeve 20 and held against the constriction at the end 20a. A piezo-electric element 22, which serves as an acceleration pickup, has a nearly punctiform contact with a point 21b of the ball 21. The piezo-electric element is connected to a contact member 23 to which the signal line or lead 24 is connected. A thrust member 26, which is provided with external threads 27, is threaded into an insulating part or sleeve 25. By threading the member 26 into the sleeve 20, the insulating part 25 moves the piezo-electric element 22 into contact with the ball 21 and hold it against the end 20a. The external threads 27 of the thrust member 26 enable mounting the test head into a bore at the end 2a of the ram 2.

The ram 2 between the end 2a and a radial opening 28 has a hollow channel 29. The signal line 24 as well as a ground line 31 extend from the test head 5 in the channel 29 to the opening 28. After exiting radially through the opening 28, the lines 24 and 31 are wound in a helical fashion around the ram over a section or distance 30 which extends up to the bearing 3. From here, the two lines pass through one of the air compensation openings 14 in the bearing 3 and extend to the plug-type couplings 12 and 13. The plug-type couplings 12 and 13 connect the lines 24 and 31 to lines 17 and 18 which extend through the hose or cord 10 to a corresponding evaluation electronics which is provided externally of the instrument 100.

The signal lines 24 and 31 are advantageously composed of an insulated stranded wire having two twisted individual wires. In an alternative construction, a thin coaxial cable can also be utilized.

The helical winding of the lines 24 and 31 within the area or section 30 occurs after the lines have been conducted through the opening 28 and after the test head 5 has been screwed into the ram 2. In order to facilitate assembly, a plug-type connection can also be provided at the connecting location.

In its built-in condition, the line section 30 lies against a detent or shoulder 32 of the bearing 3 and is compressed to such a degree that a prestress force $F_V$ is formed by the windings. This prestress force $F_V$ corresponds to a frictional force $F_R$ between the ram 2 and the bearings 3 and 4 and is directed opposite to this force when the ram is moved in a forward direction. The frictional force between the bearings and rams is thereby largely compensated by the prestress force $F_V$. The prestress path $s_v$ of the spring is far greater than the stroke of the ram 2 so that the spring power remains approximately constant over the entire length of the stroke of the ram.

A modification of the back instrument part 1b of FIG. 2 is shown by the back instrument part 1b' in FIG. 5. A magnetic coil 8 is situated in the housing part 1b' in a partially axially projecting fashion and is surrounded by flux-directing elements 40 of soft iron material which are held in the housing part 1b' by means of an insulating sleeve 41. Part of the insulating sleeve 41 projects from the housing part 1b' and forms a center plug sleeve for forming a mechanical connection to a sleeve-shaped end of a housing part 1a' (see FIG. 6). The element 40 is composed of two longitudinally extending sections or segments 40a and 40b which are electrically insulated from one another by means of a suitable insulating means and these sections 40a and 40b include connection members 42a and 42b at their back end for the connection of two lead-in signal lines 17 and 18. In the coupled condition, the sections 40a and 40b interconnect the lines 17 and 18 of the instrument section 1b' to the lines 24 and 31 of the instrument section 1a'. For this purpose, the ends of the lines 24 and 31 are provided with resilient contact tongues 43a and 43b (FIG. 6). When the part 1a' is slipped onto the part 1b', the contact tongues 43a and 43b, which extend through a bearing insert 3', come into engagement in the sense of a mutual contacting with the cooperating contact surfaces 44a and 44b of the segments 40a and 40b which project axially ahead of the end of the coil 8'.

When more than two lines are required, then a correspondingly greater number of sections or segments, which extend parallel to the axis and are electrically insulated from one another, are provided. For a better contacting, the contact surfaces 44a and 44b of the segments or elements 40a and 40b are coated with a suitable contacting material at least in the front projecting region and this material is selected from a group consisting of nickel, silver and platinum.

A significant advantage of the disclosed arrangement is that the electrical connection of the connecting lines to the lines which lead to the front instrument part is resolved in a fashion which simultaneously improves the magnetic properties of the drive coil. In that the iron sleeve or ring provided for improving the magnetic properties of the drive coil is also co-employed for electrical contacting, a structurally simpler format and an increased operational reliability can be achieved in addition to the advantages already mentioned.

The control of the drive for shifting the ram 2 axially and thus the speed of the ram as well as the signal evaluation for the acceleration pickup element 22 occurs in a known manner as disclosed in the above-mentioned U.S. Pat. No. 4,499,906, whose disclosure is incorporated herein.

Although various minor modifications may be suggested by those versed in the art, it should be understood that I wish to embody within the scope of the patent granted hereon, all such modifications as reasonably and properly come within the scope of my contribution to the art.

I claim:

1. In a dental percussion instrument having an instrument housing with a first and a second end being fashioned as a handpiece, a ram containing a test head at one end, means mounting the ram in the instrument housing with the one end extending from the first end of the housing and for axial movement between retracted and extended positions and electromagnetic drive means including an electromagnetic coil for shifting the ram axially within the housing, the improvements comprising the ram being essentially of a constant cross-sectional construction over its entire length and having a permanent magnet mounted at another end facing away from the test head, and wherein said drive means includes the permanent magnet coacting with the electromagnetic coil, said electromagnetic coil being mounted in the instrument housing adjacent the second end and in an axially spaced position relative to the other end of the ram and the permanent magnet, whereby the housing adjacent the first end has a slim configuration approaching the size of the one end of the ram.

2. In a dental percussion instrument according to claim 1, wherein the instrument housing is divided into a front section and a back section connected to one another by a releasable connection, and wherein said magnetic coil forms an inseparable unit with a back section and the ram is mounted in the front section.

3. In a dental percussion instrument according to claim 2, wherein a supply line is inseparably connected to the back section of the instrument housing.

4. In a dental percussion instrument according to claim 2, wherein the magnetic coil is surrounded by a flux-concentrating element composed of a plurality of segments extending parallel to the axis of the coil and being insulated from one another, said segments having contact surfaces for engaging contacts of electrical leads in the front section so that when the back and front sections are connected together electrical contact is established through the segments.

5. In a dental percussion instrument according to claim 4, wherein the segments forming the flux-concentrating element extend past an end face of the magnetic coil to form projecting ends, said projecting ends forming cooperating contacts for the contact element situated in the frong section of the instrument housing.

6. In a dental percussion instrument according to claim 5, wherein the plurality of segments forming the flux-concentrating element are surrounded by an insulating sleeve partially projecting from the back section of the instrument housing to form a projecting portion, said projecting portion of the insulating sleeve forming a center plug sleeve for connecting the two sections of instrument housing together.

7. In a dental percussion instrument according to claim 4, wherein each of the contact surfaces of the segments are provided with a coating of contact material at least in the region of contact.

8. In a dental percussion instrument according to claim 1, wherein the means for mounting comprise at least one sliding bearing having at least one axial opening.

9. In a dental percussion instrument according to claim 8, wherein said ram has a guide channel preferably essentially situated and extending from said test head over a significant part of the ram length, said guide channel receiving signal lines extending to an acceleration pickup provided in the test head.

10. In a dental percussion instrument according to claim 9, wherein the ram has a radial opening extending to the guide channel, said signal lines being conducted in the channel to the radial opening, then radially out of the radial opening and wound around said ram in a helical fashion over a prescribed length.

11. In a dental percussion instrument according to claim 10, wherein the signal lines have a spring property and the winding of the signal lines over a prescribed length forms an insulated spring.

12. In a dental percussion instrument according to claim 11, wherein the signal lines are two wires stranded together to form a stranded wire.

13. In a dental percussion instrument according to claim 11, wherein one end of the spring is held against a shoulder in a prestressed condition so that as the ram moves from the retracted position to the extended position, the prestressed force of the spring compensates for the frictional force between the ram and the mounting means.

14. In a dental percussion instrument according to claim 13, wherein the prestress path of the spring formed by the signal lines is far greater than the length of the maximum stroke of the ram so that the prestress force is substantially constant during travel of the ram between the retracted and the extended positions.

* * * * *